US006977269B1

(12) United States Patent
Saunders et al.

(10) Patent No.: US 6,977,269 B1
(45) Date of Patent: Dec. 20, 2005

(54) METHOD OF IMPROVING ANIMAL TISSUE QUALITY

(75) Inventors: Court A. Saunders, Clive, IA (US); Fred R. Wolf, West Des Moines, IA (US); Thomas E. Sauber, Johnston, IA (US); Fredric N. Owens, West Des Moines, IA (US)

(73) Assignee: Pioneer Hi-Bred International, Inc, Des Moines, IA (US)

( * ) Notice: Subject to any disclaimer, the term of this patent is extended or adjusted under 35 U.S.C. 154(b) by 342 days.

(21) Appl. No.: 10/136,472

(22) Filed: May 1, 2002

Related U.S. Application Data

(60) Provisional application No. 60/288,336, filed on May 3, 2001.

(51) Int. Cl.[7] .......................................... A61K 31/355
(52) U.S. Cl. ..................................................... 514/458
(58) Field of Search ......................................... 514/458

(56) References Cited

U.S. PATENT DOCUMENTS

| | | | |
|---|---|---|---|
| 4,594,437 A | 6/1986 | Sampathkumar | 549/413 |
| 5,427,802 A | 6/1995 | Evans et al. | 426/2 |
| 5,705,206 A | 1/1998 | Ashes et al. | 426/2 |
| 5,851,572 A | 12/1998 | Cook et al. | 426/2 |
| 5,871,795 A | 2/1999 | Roth | 426/319 |
| 6,060,087 A | 5/2000 | Cook et al. | 426/2 |
| 6,103,276 A | 8/2000 | Pilgrim et al. | 426/2 |
| 6,262,109 B1 | 7/2001 | Clark et al. | 514/458 |
| 6,362,221 B1 | 3/2002 | Clark et al. | 514/458 |

FOREIGN PATENT DOCUMENTS

| | | | | |
|---|---|---|---|---|
| WO | 96/19217 | 6/1996 | ........ | A61K 31/355 |
| WO | 99/04622 | 2/1999 | ............ | A01H 5/00 |
| WO | 00/08190 | 2/2000 | .......... | C12N 15/82 |
| WO | 02/33060 | 4/2002 | ............ | C12N 9/00 |

OTHER PUBLICATIONS

Agricola AN 2001:80572, Walton et al, British poultry science, Mar. 2001, 42(1), 123-129, abstract.*
Frosti AN 463698, Ackman et al, Flavor and lipid chem. of seafoods:proceedings of a symposium, Orlando, Aug. 1996, published by ACS, Washington, D.C., 1997, 148-165, abstract.*
FSTA, AN 1997(07):R0057, Parazo, Dissertation Abstracts International, B, 1996, thesis publ. 1995 57(4) 2238-2239. 191 pp, abstract.*
Robert J. Grebenok, et al., "Characterization of Zea mays endosperm C-24 sterol methyltransferase: one of two types of sterol metyltransferase in higher plants", *Plant Molecular Biology* (1997), 34:891-896.
C. Faustman et al., "New Developments in Vitamin E Nutrition and Meat Quality" 157-164. 1998.

Kazuo Mukai, , et al., "Kinetic Studies of Antioxidant Activity of New Tocopherol Model Compounds in Solution", *Bull. Chem. Soc.* (1987), 60:2163-2167.
G. W. Burton et al., "Autoxidation of Bilogical Molecules. 1. The Antioxidant Activity of Vitamin E and Related Chain-Breaking Phenolic Antioxidants in Vitro[1]", *J. Am. Chem. Soc., Health & Nutrition* (1981), 103:6472-6477.
Edwin N. Frankel, "Antioxidants and Hydroperoxides: From Soybean Oil to Red Wine",*Inform.* (1999), 889-896.
Anna-Maija Lampi et al., "Effect of a- and y-Tocopherols on Thermal Polymerization of Purified High-Oleic Sunflower Triaclyglycerols", *JAOCS* (1998), 1699-1703.
L. Lakritz et al., "Effect of Ionizing Radiation on Unesterified Tocopherols in Fresh Chicken Breast Muscle", *Meat Science* (1992), 32:257-265.
Anna-Maija Lampi, , et al., , "Antioxidant Activity of Minor Amounts of y-Tocopherol in Natural Triacylglycerols", *JAOCS* (1997), 549-555.
T. Gattstein et al., , "Model Study of Different Antioxidant Properties of a- and y-Tocopherol in Fats", *Fat. Sci. Technol.* (1990), 139-144.
Claus Jensen, , et al., "Supplementation of Broiler Diets with All-Rac-a- or a Mixture of Natural Source RRR-a,y-Tocopheryl Acetate. 2. Effect on the Oxidative Stability of Raw and Precooked Broiler Meat Products", *Poultry Science* (1995), 2048-2056.
Peter P. Hoppe, "Comparison of Plasma a- and y-Tocopherols After Oral and Intramuscular Administration of RRR-a-Tocopherol or RRR-y-Tocopherol to Weanling Pigs", *Internat. J. Vit. Nutr. Res.* (1991), 114-119.
Willy A. Behrens et al., "Mechanisms of Absorption, Transport and Tissue Uptake of RRR-a-Tocopherol and d-y-Tocopherol in the White Rat[1,2]", *American Institute of Nutrition* (1987), 1562-1568.
Michel Clement, et al., "Uptake of Dietary RRR-a- and RRR-y-Tocopherol by Nervous Tissues, Liver and Muscle in Vitamin-E-Deficient Rats", *Elsevier Science* (1995), 175-180.
Maret G. Traber et al., "Preferential Incorporation Of A-Tocopheral Vs Y-Tocopherol In Human Lipoproteins [1-3]", *American Society for Clinical Nutrition* (1989), 517-526.
A.K. Dutta-Roy, "Molecular Mechanism of Cellular Uptake and Intracellular Translocation of a-Tocopherol: role of Tocopherol-binding Proteins", *Food and Chemical Toxicology* (1999), 967-971.

(Continued)

*Primary Examiner*—Rebecca Cook
(74) *Attorney, Agent, or Firm*—Steven J. Callistein; Kathryn K. Lappegard; Pioneer Hi-Bred International, Inc.

(57) ABSTRACT

A novel method for improving the tissue quality of an animal is provided. The method comprises feeding the animal a diet supplemented with gamma-tocopherol in an amount effective to improve the tissue quality. The gamma-tocopherol may be fed alone or in combination with other antioxidants, such as alpha-tocopherol. The method may be practiced on ruminants and non-ruminants.

38 Claims, No Drawings

OTHER PUBLICATIONS

Regina Brigelius-Flohe et al., "Vitamin E: Function and Metabolism", *The FASEB Journal* (1999), 1145-1155.

Khai Tran et al., "Comparative Uptake and a- and y-Tocopherol by Human Endothelial Cells", *LIPIDS* (1992), 38-41.

Maret G. Traber, et al., "Absorption of Water-Miscible Forms of Vitamin E in a Patient with Cholestasis and in Thoracic Duct-Cannulated Rates[1-3]", *American Journal of Clinical Nutrition* (1986), 914-923.

Regina Brigelius-Flohe et al., "Vitamine E: Function and Metabolism", *FASEB J.* (1999), 1145-1155.

Maret G. Traber et al., "Preferential Incorporation of a-Tocopherol vs y-Tocopherol in Human Lipoproteins[1-3]", *American Society for Clinical Nutrition* (1989), 517-526.

Eric A. Decker, et al., "Improvement of Oxidative Stability of Beef and Lamb with Vitamin E", *Antioxidants in Muscle Foods*, 231-261, 2000.

Eric A. Decker, et al., "Dietary Delivery Versus Exogenous Addition of Antioxidants", *Antioxidants in Muscle Foods*, 315-343, 2000.

Eric A. Decker, et al., "Dietary Treatment and Quality in Mediterranean Meat Products", *Antioxidants in Muscles Foods*, 350-363, 2000.

* cited by examiner

METHOD OF IMPROVING ANIMAL TISSUE QUALITY

CROSS-REFERENCE TO RELATED APPLICATION

This application claims priority to and the benefit of U.S. Provisional Application No. 60/288,336 filed May 3, 2001.

BACKGROUND

1. Field of the Invention

This patent relates to a method of improving animal tissue quality. More specifically, this patent relates to a method of improving animal meat tissue quality by administering to the animal effective amounts of gamma-tocopherol.

2. Description of the Related Art

Consumers have become increasingly demanding of higher quality cuts of meat. For consumers, one major indicator of meat quality is visual appearance. With regard to beef, most consumers associate quality with the bright red color produced by the oxymyoglobin pigment. Unfortunately, oxymyoglobin is susceptible to oxidation. Within days of slaughter, oxygen exposure causes the oxymyoglobin to oxidize into metmyoglobin, turning the beef from bright red to a less appealing brownish color. Color is also important for pork with a reddish-pink color preferred. In addition, a key determinant of pork quality is the presence of exudate ("purge") in the retail package resulting from the release of intracellular water due to protein denaturation and loss of cell wall integrity. Excessive purge results in economic loss to meat processors and a reduction in consumer value.

Research has shown that supplementing an animal's diet with antioxidants and, in particular, alpha-tocopherol acetate, can protect the slaughtered meat from oxidation, purge and discoloration. Consequently, meat producers may incorporate antioxidants into their animals' diets to increase the amount of antioxidants in the meat which, in turn, prolongs the shelf life of the meat.

Previous research indicates that supplementation of vitamin E in the form of alpha-tocopherol acetate at supranutritional levels is an effective means for improving meat quality (Faustman and Lynch, New Developments in Vitamin E Nutrition and Meat Quality, presented at Western Nutrition Conference, Saskatoon, Canada, 1998). In addition to improved color, supplementation of animal diet with alpha-tocopherol acetate results in improved stability of membrane bound lipids, maintenance of integrity of cellular membranes, and reduced purge (Monahan, F. J., et al., Food Chem. 1993).

Supranutritional vitamin E supplementation has been shown to be effective for turkeys and broilers (Marusich, et al., 1975), laying hens (Combs and Regenstein, 1980), veal calves (Igene, et al., 1976), horses (Yamauchi, et al., 1977), catfish (O'Keefe and Nobel, 1978), rainbow trout (Boggio, et al., 1985), swine (Asghar, et al., 1989), lambs (Strohecker, et al., 1997), and beef cattle (Faustman, et al., 1989). An extensive analysis of the benefits and mechanisms of vitamin E supranutritional supplementation is provided in Decker, E., Faustman, C. and Lopez-Bote, C., Antioxidants in Muscle Foods, John Wiley and Sons, Inc., 2000. Table 12-1 of Antioxidants in Muscle Foods contains a list of supranutritional vitamin E supplementation studies for various species, with effect, dosage and duration information noted, and Table 12-1 and the references cited therein are specifically incorporated by reference herein.

On a commercial scale, beef cattle feedlot nutritionists desire to achieve a total supplemental intake of vitamin E during the total feedlot period of about 50,000 IU/KG over a minimum of about 45 days. This can be accomplished with varying dosage levels and durations. For example, 500 IU/KG of vitamin E per steer daily for 126 days yielded this level (Liu, Q., et al., 1996, Titration of Fresh Meat Color Stability and Malondialdehyde Development with Holstein Steers Fed Vitamin E Supplemented Diets, J. Anim. Sci. 74:117–126), resulting in a total intake of 63,000 IU/KG and tissue level of 2.5 mg/g. Similarly, 1300 IU/KG of vitamin E per steer fed daily for 44 days resulted in a total intake of 57,200 IU/KG and a tissue level of 3.3 mg/g, while 400 IU/KG of vitamin E per steer fed daily for 180 days resulted in a total intake of 72,000 IU/KG and the same tissue level of 3.3 mg/g (Arnold, R., et al., 1993, Dietary a-Tocopherol Acetate Enhances Beef Quality in Holstein and Beef Bred Steers, J. Food Sci. 58:28–33). For exported beef, where storage times are longer, it is suggested that 2000 IU/KG of vitamin E per steer be fed daily for 100 days. This resulted in tissue levels of 6.1 mg/g (Sanders, S., et al., 1997, Vitamin E Supplementation of Cattle and Shelf-life of Beef for the Japanese Market, J. Anim. Sci. 2634–2640). Commercial supranutritional feeding levels of alpha-tocopherol for swine is approximately 200 IU/KG per animal on a daily basis for 100 days. This dosage level and duration may be varied to obtain a similar total intake as described for beef above.

While dietary supplementation with the antioxidant alpha-tocopherol has proven to be an effective means for improving meat quality, there remains a need to further improve meat quality.

Gamma-tocopherol has heretofore been known to be a weaker in vivo antioxidant than alpha-tocopherol. In vivo studies on iron-loaded rats have demonstrated the antioxidant efficacy of gamma-tocopherol to be about one-third that of alpha-tocopherol on a per unit mass basis as determined by their ability to inhibit lipid peroxidation (Dillard et al., 1983, Relative Antioxidant Effectiveness of Alpha-tocopherol and Gamma-tocopherol in Iron Loaded Rats, J. Nutr. 113: 2266–2273). It was also shown that gamma-tocopherol was not retained in the blood stream as well as alpha-tocopherol and suggested that the liver preferentially eliminates gamma-tocopherol, while alpha-tocopherol is transported to tissues via an alpha-tocopherol specific lipoprotein (Traber, et al., 1989, Preferential Incorporation of Alpha-tocopherol vs. Gamma-tocopherol in Human Lipoproteins, Am. J. Clin. Nutr. 49:517–526). It is also well known that only about 3–19% of gamma-tocopherol is absorbed in the bloodstream, as compared to about 100% of alpha-tocopherol (Lynch, G. L., et al., 1991, Vitamin E Structure and Bioavailability: Vitamin E in Animal Nutrition and Management, BASF Corp., Parsippany, N.Y., pp. 1–6). Additionally, certain in vitro studies have shown alpha-tocopherol to be a more effective antioxidant than beta, gamma and delta-tocopherol (See Burton, G., et al., 1981, Autoxidation of Biological Molecules: The Antioxidation Activity of Vitamin E and Related Chain-Breaking Phenolic Antioxidants in Vitro, J. Am. Chem. Soc. 103:6472–6477 and also Mukai, K., et al., 1987, Kinetic Studies of Antioxidant Activity of New Tocopherol Model Compounds in Solution, Bull. Chem. Soc. Jpn., 60:2163–2167). These articles, and the fact that gamma-tocopherol is a biological precursor to alpha-tocopherol, have led those of skill in the art to believe that gamma-tocopherol is less effective than alpha-tocopherol in improving meat quality. In fact, despite extensive analysis of alpha-tocopherol in feeding studies, the effect of dietary gamma-tocopherol supplementation on tissue quality, such as meat, has not been evaluated in feeding studies.

Thus it is an object of the present invention to provide a method for improving the tissue quality of an animal. It is a further object to improve meat tissue, especially its water-holding capacity (as estimated from pH) and its shelf life (as measured by color change and lipid peroxidation as measured by and change of TBA number over time).

Another object of the present invention is to provide a method for improving tissue quality over that already achieved through diet supplementation with alpha-tocopherol.

Further and additional objects will appear from the description and appended claims.

SUMMARY OF THE INVENTION

The present invention is a method for improving the tissue quality of an animal, comprising feeding the animal a diet including gamma-tocopherol in an amount effective to improve the tissue quality. The quality of meat tissue may be measured as prolonged shelf life, reduced oxidation, higher pH, improved color and reduced purge. The gamma-tocopherol may be in the form of a distillate obtained from oil seed processing, 6-hydroxy-2,7,8-trimethylchroman-2-carboxylic acid (gamma-tocopherol without the hydrophobic side chain), gamma-tocopherol acetate (gamma-tocopherol acetylated for stability), and/or produced by a plant transgenically modified to produce high levels of gamma-tocopherol. The animal may be a ruminant, such as bovine or lamb, or non-ruminant, such as swine, poultry or fish. Bovine includes, but is not limited to, beef cattle, dairy cattle and bison. Poultry includes, but is not limited to, broilers, layer hens, turkey, ostriches and emu.

The diet may comprise between 100 ppm to 1,000 ppm gamma-tocopherol, although 150 ppm to 450 ppm is preferred. In special circumstances, such as for meat tissue intended for the export market or supplementation for calving dairy cattle, up to 4,000 ppm gamma-tocopherol is preferred. The diet may also contain alpha-tocopherol or other antioxidants. The amount of gamma-tocopherol in the diet should preferably, but not necessarily, result in a concentration of gamma-tocopherol of at least 0.8 mg/kg in animal tissue and, more preferably, at least 1.0 mg/kg tissue.

DETAILED DESCRIPTION OF THE INVENTION

Gamma-tocopherol (y-tocopherol) has heretofore been believed to be a weaker anti-oxidant than alpha-tocopherol (α-tocopherol) on a per unit mass basis and thus, less effective as a dietary supplement for animals. It was also shown that gamma-tocopherol was not retained in the bloodstream as well as alpha-tocopherol and thus, one would not expect that gamma-tocopherol would have a significant effect on tissue quality. However, until now, the effect of dietary gamma-tocopherol supplementation on tissue quality has not been evaluated. Applicants have found that, surprisingly, supplementation of animal diets with gamma-tocopherol results in statistically significant improvements in certain tissue quality parameters. Supplemental gamma-tocopherol is the amount of gamma-tocopherol added to a diet in excess of the amounts that are provided in a normal diet.

The present invention is a novel method for improving the tissue quality of an animal, comprising feeding the animal a diet including gamma-tocopherol in an amount effective to improve the tissue quality. The amount of gamma-tocopherol in the diet is preferably that which results in a concentration of gamma-tocopherol of at least 0.8 mg/kg tissue and, more preferably, at least 1.0 mg/kg tissue. In the examples that follow, meat tissue quality is measured in various ways, including higher pH, greater oxidative stability, and slower fade from red. The present invention has been proven effective with both ruminants and non-ruminants. The improved tissue may comprise any animal tissue, and includes muscle meat, organs, milk and eggs.

The present invention is further defined by the following examples. These examples, while indicating preferred embodiments of the invention, are given by way of illustration only. From the discussion contained herein and the examples themselves, one skilled in the art can ascertain the essential characteristics of the invention and, without departing from the spirit thereof, can make changes and modifications to the invention to adapt it to various situations and conditions.

EXAMPLE 1

Demonstration that Supplementation Of Swine Diet With Gamma-Tocopherol Results in Statistically Significant Improvements in Meat Quality Parameters Applicants assessed the effects of gamma-tocopherol supplementation on meat quality in an experiment in which pork from pigs fed one of three dietary concentrations of gamma-tocopherol was compared to pork from pigs fed either no supplemental tocopherol in excess of amounts needed to support growth and development, or one of three dietary concentrations of alpha-tocopherol.

Young pigs were fed a diet containing 15 IU/kg feed (=15 mg/kg feed=1 ppm) vitamin E (in the form of alpha-tocopherol acetate) up to 120 pounds. Upon reaching 120 pounds, the pigs were randomly assigned to treatments using weight as a blocking factor. Sixteen pigs were allocated to the control diet, while thirteen pigs were allocated to each test diet. Treatments consisted of typical corn-soybean meal based diets with three levels of dietary tocopherol: (1) Control diet (15 mg/kg feed alpha-tocopherol acetate); (2) diets supplemented with 150, 300 or 450 mg/kg feed alpha-tocopherol acetate; and (3) diets supplemented with 150, 300 or 450 mg/kg feed gamma-tocopherol. Diets were formulated to provide adequate levels of all nutrients and fed in four phases. A lab analysis confirmation of the feed samples showed actual values of 134 ppm, 274 ppm and 456 ppm for the three gamma-tocopherol diets, and less than 10 ppm of gamma-tocopherol in the three alpha-tocopherol samples.

The levels of alpha-tocopherol supplementation chosen were those previously shown to improve meat quality and the pigs consuming these diets were used as positive controls. Pigs consuming diets without additional supplementation of alpha or gamma-tocopherol were used as negative controls. Pork quality was assessed using standard methods, including pH, Japanese color score, oxidative stability, retail display appearance and Minolta color values.

Pigs were weighed and feed intake was determined at 14-day intervals and on the day prior to slaughter. Blood samples were collected prior to the start of the treatment diets, on each weigh date, and on the day prior to slaughter to determine serum concentrations of alpha- and gamma-tocopherol.

The trial was terminated when the average weight of a treatment replicate reached 260 pounds (minimum of 60 days). Standard carcass data (hot carcass weight, backfat, loin depth and lean) were collected. In addition to the standard carcass data collected at the slaughter plant, color, pH, marbling, firmness and Hunter Lab data were collected. Loin and ham samples were also collected for determination of gamma-tocopherol concentration.

Pork chops (2.5 cm) were cut from vacuum-packaged pork loins that had been stored for 21 days at 1 degree C. Freshly cut chops were placed on styrofoam trays with DriLoc (V 50 pads) and overwrapped with PVC (23,250 cc/m 2 /24 hours oxygen permeability). Pork chops were placed in simulated retail display at 2±3 degrees C. for six days. Product temperature was monitored during the display period. Chops were analyzed for lightness (L*), redness (a*), and yellowness (b*) using Illuminant C or D65 on a Minolta Chroma Meter. Three readings per chop were taken on display days 0, 1, 2, 3, 4 and 5.

Loin chop color was evaluated using a trained visual panel of 10 people. Color score was determined using a five-point scale with a score of one (1) representing a very bright pinkish gray and a score of five (5) representing a dull dark red to brown color representative of color deterioration.

Determination of pH was made on days 0 and 5 as an indication of pork spoilage. Oxidative rancidity was measured using 2-Thiobarbituric acid to determine TBA number. Final values were expressed as mg malonaldehyde per 1000 grams of meat. Purge was determined on the vacuum-packaged pork loins.

Data were analyzed using the GLM procedure of SAS. Due to a limited number of observations from the 150 IU alpha-tocopherol treatment, no estimates of carcass or loin quality measures are presented for that treatment. Data collected over a period of days were also analyzed as a splitplot. Contrasts were made between the Control and added tocopherol diets, Control and alpha-tocopherol, Control and gamma-tocopherol, and alpha- versus gamma-tocopherol.

A summary of the results is presented in Tables 1 and 2:

TABLE 1

COMPARISON OF PORK QUALITY FOR CONTROL, ALPHA-TOCOPHEROL AND GAMMA-TOCOPHEROL GROUPS

| Criteria | Control | a-Tocopherol | γ-Tocopherol | Contrasts (P value) | | | |
|---|---|---|---|---|---|---|---|
| | | | | Control vs Tocopherol | Control vs a-Tocopherol | Control vs γ-Tocopherol | a-vs γ-Tocopherol |
| PH | 5.76 | 5.97 | 6.11 | .01 | NS | .003 | NS |
| Japanese Color Score | 3.12 | 3.75 | 3.94 | .03 | NS | .02 | NS |
| Oxidative stability (5 day storage TBA) | .216 | .103 | .102 | .03 | NS | NS | NS |
| Appearance score (after 5 day retail display) | 3.58 | 3.79 | 3.89 | NS | NS | NS | NS |
| Minolta L* values (after 5 day retail display) | 45.8 | 43.6 | 41.4 | .002 | NS | .0001 | NS |
| Minolta a* values (after 5 day retail display) | 8.29 | 7.49 | 8.13 | NS | NS | NS | NS |
| Minolta b* values (after 5 day retail display | 6.55 | 4.95 | 4.48 | .001 | .006 | .0001 | NS |

TABLE 2

COMPARISON OF PORK QUALITY AT VARIOUS DIETARY SUPPLEMENT LEVELS

| Criteria | Control | Alpha-tocopherol Level | | | Gamma-tocopherol Level | | | SEM |
|---|---|---|---|---|---|---|---|---|
| | | 150IU | 300 IU | 450 IU | 150 IU | 300 IU | 450 IU | |
| PH | 5.76$^b$ | Non-est | 6.08$^{ab}$ | 5.85$^b$ | 5.99$^{ab}$ | 6.28$^a$ | 5.94$^b$ | 0.18 |
| Japanese Color Score | 3.12$^b$ | Non-est | 3.56$^{ab}$ | 3.94$^{ab}$ | 3.18$^{ab}$ | 4.32$^a$ | 3.56$^{ab}$ | 0.57 |
| Oxidative stability (5 day storage TBA) | .216 | Non-est | .134 | .072 | .177 | .080 | .125 | 0.76 |
| Appearance score (after 5 day retail display) | 3.58 | Non-est | 3.49 | 4.09 | 4.05 | 4.06 | 3.72 | 0.32 |
| Minolta L* values (after 5 day retail display) | 45.8$^a$ | Non-est | 45.3$^{ab}$ | 41.9$^{bc}$ | 42.4$^{bc}$ | 39.7$^c$ | 43.0$^b$ | 1.70 |

TABLE 2-continued

COMPARISON OF PORK QUALITY AT VARIOUS DIETARY SUPPLEMENT LEVELS

| Criteria | Control | Alpha-tocopherol Level | | | Gamma-tocopherol Level | | | SEM |
|---|---|---|---|---|---|---|---|---|
| | | 150IU | 300 IU | 450 IU | 150 IU | 300 IU | 450 IU | |
| Minolta a* values (after 5 day retail display) | 8.29$^a$ | Non-est | 8.40$^a$ | 6.58$^b$ | 7.57$^{ab}$ | 8.20$^a$ | 8.05$^a$ | 0.57 |
| Minolta b* values (after 5 day retail display) | 6.55$^a$ | Non-est | 5.93$^{ab}$ | 3.97$^{bc}$ | 5.13$^{bc}$ | 3.85$^c$ | 5.12$^{bc}$ | 0.73 |

SEM = Standard Error of Measurement
Means within same row with unlike superscript differ P < 0.05

Referring to Table 1, adding either alpha- or gamma-tocopherol to the diet of pigs increased pH in the pork loin from the control level of 5.76. However, the pH was greatest (representing highest quality) in loin from pigs fed gamma-tocopherol (6.11 compared to 5.97 for pigs fed alpha-tocopherol). This surprising result indicates that supplementation of swine diet with gamma-tocopherol can improve meat quality better than supplementation with alpha-tocopherol.

Minolta a* value is an indication of redness. A higher a* value after five days of storage indicates less fading and thus, improved quality. Surprisingly, adding gamma-tocopherol resulted a pork loin with a higher Minolta a* value than the pork loin from the alpha-tocopherol group (8.13 vs. 7.49).

The right-hand side of Table 1 shows the statistical significance of the comparison data. Contrast P values of less than 0.05 are considered statistically significant. Thus, compared to the control, tocopherol supplementation resulted in statistically significant differences in four of the seven meat quality indicators. Supplementation with alpha-tocopherol resulted in a statistically significant improvement in only one measurement, Minolta b* value. Surprisingly, supplementation with gamma-tocopherol resulted in statistically significant improvements in four measurements: pH, Japanese color score and Minolta L* and b* values.

Referring to Table 2, the data suggests that maximum effect of gamma-tocopherol is achieved at a dietary supplementation level of 300 IU/kg. At this level, pH was higher than for any other group, including the group fed alpha-tocopherol. Minolta a* value was higher at 300 IU/kg gamma-tocopherol (8.40) than for any group except the control group (8.29). Similarly, the value for oxidative stability after five days (0.080), representing the level of lipid oxidation, was lowest (best) for the swine fed 300 IU/kg gamma-tocopherol than for the swine fed 300 IU/kg alpha-tocopherol.

The level of gamma-tocopherol in the feed was between 150 ppm and 450 ppm, with the best results being at 300 ppm. It is expected that benefits in meat quality will be seen at other levels as well, from as low as 50 ppm to as high as 4000 ppm.

It is further contemplated that supplementation of animal feed with both alpha and gamma-tocopherol, or with gamma-tocopherol and other anti-oxidants such as alpha lipoic acid, coenzyme Q10, glutathione and ascorbic acid, will also provide improvements in meat quality.

EXAMPLE 2

Demonstration that Meat Quality is a Function of Concentration of Gamma-Tocopherol in Swine Tissue Table 3 illustrates the effect on pH of alpha, gamma and total tocopherol levels in the pork loin. The data was derived from the same swine tests as in Example 1. Data from 43 samples was ranked in descending order for four parameters: alpha-tocopherol concentration, gamma-tocopherol concentration, alpha plus gamma-tocopherol concentration, and ratio of alpha-tocopherol to gamma-tocopherol. The data was divided into four quartiles, averaged, and compared to the corresponding quartile loin pH average.

The data shows that the clearest positive effect on pH is obtained by increasing the level of gamma-tocopherol in the tissue. Increasing the level of gamma-tocopherol from 0.35 mg/kg tissue to 2.78 mg/kg tissue increased pH from 5.77 to 6.03, indicating that supplementation of animal diet with gamma-tocopherol enhances meat quality better than supplementation with alpha-tocopherol, which did not show the same increase in pH. A gamma-tocopherol to alpha-tocopherol ratio of 1.45 showed the greatest increase in pH (6.07). A gamma-tocopherol to alpha-tocopherol ratio of one or more would be preferred for use in the present invention.

The amount of gamma-tocopherol in the diet may be adjusted to that which results in a concentration of gamma-tocopherol in the animal tissue of at least 0.8 mg/kg tissue. Levels of gamma-tocopherol in the animal tissue of 1.0 to 1.3 mg/kg or more were found to further improve meat quality, as measured by loin pH.

TABLE 3

QUARTILE AVERAGES FOR SELECTED LOIN TOCOPHEROL CONCENTRATIONS (mg/kg tissue) VERSUS LOIN PH

| | Alpha-Toco/pH | Gamma-Toco/pH | Alpha-T + Gamma-T/pH | Gamma-T: Alpha-T/pH |
|---|---|---|---|---|
| 1$^{st}$ Q | 4.80/5.80 | 2.78/6.03 | 5.77/5.84 | 1.45/6.07 |
| 2$^{nd}$ Q | 2.64/5.78 | 1.33/5.95 | 4.59/5.96 | 0.86/5.90 |
| 3$^{rd}$ Q | 1.76/6.01 | 0.62/5.77 | 3.25/6.01 | 0.27/5.74 |
| 4$^{th}$ Q | 1.28/5.93 | 0.35/5.77 | 2.11/5.72 | 0.09/5.79 |

A significant effect was also noted for overall aerobic plate count, calculated as $Log_{10}$ $CFU/CM^2$. Lactic acid bacteria population was significantly higher for loins from the 300 gamma-tocopherol treatment ($2.13 \times 10^2$) as compared with loins from control ($1.81 \times 10^1$), the 450 IU/kg alpha-tocopherol treatment (6.84×10⁰), the 450 IU/kg gamma-tocopherol treatment (1.07×10¹), and a significantly higher lactic acid bacterial population was observed with the added gamma-tocopherol group as a whole. This indicates that gamma-tocopherol also increases tissue quality when measured in terms of food safety and preservation.

EXAMPLE 3

Demonstration that Supplementation of Lamb Diet with Gamma-Tocopherol Enhances Meat Quality Supplementation of ruminant diets with certain fatty acids can improve muscle and adipose quality through the increase in proportions of unsaturated fatty acids (UFA). The increase in UFA content is favorable from a human health standpoint. However, fresh meat products that have a greater amount of UFA are more susceptible to oxidation. Oxidation results in a change in meat color and lowers consumer acceptance of the meat product. Addition of antioxidants, such as alpha-tocopherol acetate, to ruminant diets can protect against oxidative change in meats by increasing the level of antioxidant in muscle tissues.

The effects of diet supplementation with alpha-tocopherol and gamma-tocopherol on tissue oxidation and storage life of fresh meat from lambs fed a diet supplemented with tocopherol was studied. A total of 42 weaned Western white-faced lambs (4 ewes, 38 males) were used in a feeding trial. The lambs were housed two per pen in a slatted floor barn and initially fed chopped oat hay, then gradually acclimated to a beet pulp-based basal diet. The basal ration consisted of 82.2% beet pulp pellets, 9.5% chopped oat hay, 6.0% liquid molasses, 1.5% soybean meal, 0.8% mineralized salt, and monensin (30 g/ton). All lambs were given ad libitum access to the basal diet.

The basal diet was fed for 60 days and on days 61 and 62, lambs were weighed to calculate initial body weight. Lambs were blocked by weight, without regard to gender, and randomly assigned within weight blocks to pens, and pens were randomly assigned to dietary treatments (14 lambs/treatment).

The three dietary treatments were as follows: basal diet (Control), Control supplemented with alpha-tocopherol, and Control supplemented with gamma-tocopherol. Sunflower oil (added at 2% of daily intake) was used as a carrier to deliver the antioxidants. The oil-antioxidant preparation was thoroughly mixed into the feed ration daily and provided the equivalent of 500 IU/kg/day to each lamb. Lambs were fed their respective dietary treatments for 45 days, starting on day 63. Adjustments to feed offered were made daily based on the previous day's consumption in order to minimize feed refusal.

Interim and final weights were taken on two consecutive days after 20 and 43 days on test, respectively, to calculate average daily weight gain (ADG) and feed conversion. On the 45$^{th}$ day on test, the lambs were transported to a commercial packing plant and slaughtered the following morning. Standard carcass data were collected.

Following carcass fabrication, one boneless leg and the double loin were collected from each carcass, vacuum-packaged, transported and stored under refrigeration (2 to 4° C.) for seven days. Double-loin chops were fabricated from the semimembranosus muscle from each leg following storage. Leg and double-loin chops were wrapped in oxygen permeable fresh meat PVC film. One portion of double loin chops was displayed in a retail display case at 3 to 5° C. under continuous lighting. The leg chops and second portion of double loin chops were stored in a walk-in cooler.

After seven days in storage, the leg and loin were placed in a display case for nine days to simulate retail meat counter display conditions. Both sides of the double loin chops were evaluated on days 1, 3, 5 and 9 of retail case display for percent lean discoloration and intensity of brownness by a seven-member trained panel and also by a Spectroguard Computer Color Control System. Left and right observation values were averaged.

Leg and double loin chops were collected on days 1, 2, 3, 4, 5 and 6 of simulated meat counter storage. External fat was trimmed off the loin and leg chops and chops were analyzed for oxidation as indicated by thiobarbituric reactive substances (mg MDA×10⁶/g sample weight) and for antioxidant concentrations.

Data was analyzed by analysis of variance using SAS (v8.1, PROC MIXED) in a mixed model approach. Performance data was analyzed as a randomized complete block design with dietary treatment (TRT) and gender being used as fixed effects (wpe) while weight block (block) was considered random. For time series data without panelist involvement, data was analyzed as a split-plot design. Whole-plot was analyzed as described for performance data using TRT* block as error term while subplot fixed effects were day and wpe* day utilizing residual for error. For subjective color analysis (panelist involvement), data was analyzed as a split—split-plot design. Whole-plot was again analyzed as described for time series data. The subplot fixed effects (spe) were panelist and wpe* panelist using rt* block* gender* panelist as the error term while the sub-subplot fixed effects were day, wpe* day, and spe* day utilizing residual for error. Because of all genders not being across all treatments, the least squared means and single degree of freedom orthogonal contrasts were estimated for gender "wether" only. The orthogonal contrasts were C vs. A, C vs. G, C vs. (A+G), and A vs. G.

The results of growth performance are presented in Table 4 by period and overall. The first three columns of numbers shows growth criteria for the control group, the group whose diet was supplemented with alpha-tocopherol and the group whose diet was supplemented with gamma-tocopherol. The fourth column is standard error of measurement (SEM). The last two columns are P values for the statistical comparison of the alpha group versus the gamma group, and the control group versus the alpha and gamma groups.

As shown in Table 4, the average daily weight gain (ADG) during the second 23 days was significantly higher for lambs whose diet was supplemented with gamma-tocopherol (ADG=264.0) versus lambs whose diet was supplemented with alpha-tocopherol (ADG=190.9). This difference was statistically significant, as indicated by a contrast P value (0.0161) less than 0.05.

In the study, the lambs were fed a level of tocopherol higher than might be typically fed to ruminants to make it easier to detect differences. It is expected that lower levels would also result in meat quality responses.

TABLE 4

COMPARISON OF GROWTH PERFORMANCE IN LAMBS

| | | Treatment | | | Contrasts (P values) Control vs | |
|---|---|---|---|---|---|---|
| Criteria | Control | Alpha-tocopherol | Gamma-tocopherol | SEM | Alpha vs Gamma | Alpha & Gamma |
| Initial BW, kg | 49.5 | 48.9 | 49.6 | 3.2 | NS | NS |
| 1st 20 Days | | | | | | |
| ADG, g/d | 163.4 | 164.1 | 173.5 | 41.9 | NS | NS |
| Intake, kg/d | 1.35 | 1.43 | 1.35 | 0 | NS | NS |
| Gain: feed, g/kg | 120.6 | 124.2 | 132.6 | 31.0 | NS | NS |
| Interim BW, kg | 52.8 | 52.1 | 53.0 | 2.9 | NS | NS |
| 2nd 23 Days | | | | | | |
| ADG, g/d | 196.5[b] | 190.9[b] | 264.0[a] | 20.7 | 0.0114 | NS |
| Intake, kg/d | 1.39 | 1.54 | 1.45 | 0 | NS | NS |
| Gain: feed, g/kg | 143.9[a] | 127.1[a] | 187.2[b] | 17.4 | 0.0045 | NS |
| Final BW, kg | 57.3 | 56.6 | 59.1 | 2.9 | NS | NS |
| Overall | | | | | | |
| ADG, g/d | 181.1 | 182.3 | 221.9 | 23.6 | NS | NS |
| Intake, kg/d | 1.37 | 1.49 | 1.40 | 0 | NS | NS |
| Gain: Feed, g/kg | 133.2[ab] | 126.0[a] | 162.8[b] | 18.7 | 0.0418 | NS |

Table 5 shows the characteristics of lamb carcasses from the control group, the group whose diet was supplemented with alpha-tocopherol, and the group whose diet was supplemented with gamma-tocopherol. Characteristics included hot carcass weight, adjusted fat, rib eye area, and body wall thickness. As indicated in the last two columns under Contrasts (P values), there were no statistically significant differences (P<0.05) in carcass measurements between the alpha and gamma groups or between the control group and the alpha and gamma groups.

The fact that there were no statistically significant differences between the alpha and gamma groups suggests that gamma-tocopherol is at least as effective as alpha-tocopherol in improving carcass characteristics. Most preferred would be the addition of gamma-tocopherol to a ruminant's diet in a stabilized form, such as by encapsulating the gamma-tocopherol.

TABLE 5

COMPARISON OF CARCASS CHARACTERISTICS

| | | Treatment | | | Contrasts (P values) Control vs | |
|---|---|---|---|---|---|---|
| Criteria | Control | Alpha-tocopherol | Gamma-tocopherol | SEM | Alpha vs Gamma | Alpha & Gamma |
| Hot carcass weight, kg | 27.3 | 27.4 | 27.7 | 1.6 | NS | NS |
| Dressing percentage | 47.5 | 48.2 | 46.8 | 0.7 | 0.0819 | NS |
| Adjusted fat, cm | 0.50 | 0.55 | 0.47 | 0.09 | NS | NS |
| Rib eye area, sq. cm | 5.18 | 5.63 | 5.62 | 0.33 | NS | NS |
| Yield grade | 2.29 | 2.42 | 2.19 | 0.36 | NS | NS |
| Flank streaking[2] | 2.36[b] | 3.02[a] | 2.40[ab] | 0.27 | 0.0514 | NS |
| Bone maturity[3] | 1.66[a] | 1.47[b] | 1.62[ab] | 0.07 | 0.0940 | NS |
| Quality grade | 5.00 | 5.27 | 5.23 | 0.33 | NS | NS |
| Body wall thickness, cm | 2.05 | 2.13 | 1.92 | 0.20 | NS | NS |
| Leg score[4] | 10.9 | 10.8 | 10.8 | 0.3 | NS | NS |

[1]Means in same row with unlike superscripts differ (P < 0.05).
[2]Flank streaking: trace = 1, slight = 2, small = 3.
[3]Bone Maturity: A0 = 1.0, A10 = 1.1, A20 = 1.2, A30 = 1.3, A40 = 1.4, A50 = 1.5, A60 = 1.6, A70 = 1.7, A80 = 1.8, A90 = 1.9.
[4]Leg score: high Prime = 15, average Prime = 14, low Prime = 13, high Choice = 12, average Choice = 11, low Choice = 10, etc.

Table 6 presents coloration data for loin chops stored under simulated retail conditions. The data in Table 6 demonstrate that supplementing the diet with tocopherol (either alpha-tocopherol or gamma-tocopherol) extended shelf life beyond that of the unsupplemented (control) diet. For example, supplementation with either alpha- or gamma-tocopherol resulted in less discoloration that in the control group, although the differences were not statistically significant.

The results of loin antioxidant analyses are presented in Table 7. The data shows that antioxidant concentration was greater in the animals whose diet was supplemented with either alpha-tocopherol or gamma-tocopherol. Surprisingly, the gamma-tocopherol also resulted in an increase in loin alpha-tocopherol levels. Overall, gamma-tocopherol levels in the tissue of the animal with the gamma-tocopherol treatment was increased over 35 times (35×) the gamma-tocopherol level in the tissue of the animal fed the control treatment (6.18 vs. 0.18). A gamma-tocopherol increase of 0.5×, 1.0×, 1.5×, 2.0×, 3.0×, 4.0×, 5.0×, 7.5×, 10.0×, 15.0×, 20.0×, 25.0×, 30.0×, 35.0×, 50.0× or greater is encompassed within the present invention.

TABLE 6

COMPARISON OF LOIN CHOP COLORATION

| | Treatments | | | | Contrasts | |
| | | | | | Control vs | |
| Criteria | Control | Alpha-tocopherol | Gamma-tocopherol | SEM | Alpha vs Gamma | Alpha & Gamma |
| --- | --- | --- | --- | --- | --- | --- |
| Hunter L | 38.6$^a$ | 36.3$^b$ | 38.4$^a$ | 0.8 | .0263 | .0981 |
| Hunter a$^{2,6}$ | 10.9 | 11.9 | 11.7 | 0.5 | .8048 | .1356 |
| Hunter b$^6$ | 7.77 | 7.54 | 8.11 | 0.27 | .1290 | .8643 |
| Discoloration, %$^{2-6,8}$ | 19.7 | 12.6 | 13.7 | 3.6 | .7977 | .0997 |
| Brown color intensity$^{2-9}$ | 15.6$^a$ | 8.30$^b$ | 10.3$^{ab}$ | 2.3 | .4670 | .0152 |
| Loin MDA*, mg × 10$^6$/g$^6$ | 255.0$^a$ | 182.9$^b$ | 154.0$^b$ | 19.9 | .2415 | .0011 |
| Leg MDA, mg × 10$^6$/g$^7$ | 330.9$^a$ | 184.2$^b$ | 172.1$^b$ | 24.7 | .7260 | .0002 |

*MDA = Malondialdehyde
[1]Means in same row with unlike superscripts differ ($P < 0.05$)
[2]Sex (treatment) effect ($P < .05$)
[3]Panelist effect ($P < .0001$)
[4]Treatment × panelist effect ($P < .05$)
[5]Sex (treatment × panelist) effect ($P < .05$)
[6]Day effect ($P < .0001$)
[7]Treatment × day interaction ($P < .01$)
[8]Panelist × day interaction ($P < .0001$)
[9]Treatment × panelist × day interaction ($P < .01$)

TABLE 7

COMPARISON OF LOIN ANTIOXIDANT CONCENTRATIONS ON DAYS 1 AND 6 AND OVERALL

| | Treatments | | | | Contrasts | |
| | | | | | Control vs | |
| Criteria | Control | Alpha-tocopherol | Gamma-tocopherol | SEM | Alpha vs Gamma | Alpha & Gamma |
| --- | --- | --- | --- | --- | --- | --- |
| Day 1 | | | | | | |
| Gamma-Tocopherol, μg/g$^2$ | 0.13$^b$ | 0.30$^b$ | 7.18$^a$ | 0.32 | <.0001 | <.0001 |
| Alpha-Tocopherol, μg/g | 2.18$^b$ | 3.83$^a$ | 3.47$^a$ | 0.40 | NS | 0.0011 |
| Total, μg/g$^{3,4}$ | 2.31$^c$ | 4.13$^b$ | 10.6$^a$ | 0.57 | <.0001 | <.0001 |
| Day 6 | | | | | | |
| Gamma-Tocopherol, μg/g$^2$ | 0.24$^b$ | 0.43$^b$ | 5.57$^a$ | 0.26 | <.0001 | <.0001 |
| Alpha-Tocopherol, μg/g$^{3,4}$ | 2.43$^b$ | 6.22$^a$ | 2.87$^b$ | 0.60 | 0.0010 | 0.0099 |
| Total, μg/g$^{2,3,4}$ | 2.67$^c$ | 6.70$^b$ | 8.47$^a$ | 0.55 | 0.0186 | <.0001 |
| Overall | | | | | | |
| Gamma-Tocopherol, μg/g$^2$ | 0.18$^b$ | 0.37$^b$ | 6.38$^a$ | 0.21 | <.0001 | <.0001 |

TABLE 7-continued

COMPARISON OF LOIN ANTIOXIDANT CONCENTRATIONS ON DAYS 1 AND 6 AND OVERALL

| Criteria | Treatments | | | | Contrasts | |
| --- | --- | --- | --- | --- | --- | --- |
| | Control | Alpha-tocopherol | Gamma-tocopherol | SEM | Control vs Alpha vs Gamma | Alpha & Gamma |
| Alpha-Tocopherol, $\mu g/g^{3,4}$ | $2.31^b$ | $5.04^a$ | $3.22^b$ | 0.36 | 0.0017 | 0.0004 |
| Total, $\mu g/g^{2,3,4}$ | $2.49^c$ | $5.41^b$ | $9.57^a$ | 0.39 | <.0001 | <.0001 |

[1]Means in same row with unlike superscripts differ ($P < 0.05$).
[2]Sex (treatment) effect ($P < .05$)
[3]Day effect ($P < .05$)
[4]Treatment × day interaction ($P < 0.01$)

EXAMPLE 4

Gamma-Tocopherol Supplementation in Cattle Feed Enhances Meat and Milk Quality Currently, over 90% of the feedlot cattle and about 90% of the dairy cattle in the U.S. are fed low levels (15–60 IU/kg diet) to meet nutrient requirements (NRC, 1989; NRC, 1996). Newly stressed cattle often are fed higher levels (100 IU/kg diet). These dietary supplements are intended to meet the minimum nutrient requirements for vitamin E.

Currently about 95% of the vitamin E added to cattle feed is alpha-tocopherol in the form of alpha-tocopherol acetate. About 20% of the feedlot cattle are fed higher supranutritional levels of alpha-tocopherol acetate to lengthen the time period that beef in the meat counter stays bright red and does not develop rancid flavors during storage. This is of special concern for beef that is exported (e.g., to Japan) where beef must be stored fresh longer during transit than in the US.

One study from South Dakota indicated that shelf life of beef was longer for steaks from steers fed high oil corn than from steers fed typical corn, and this was associated with higher concentrations of tocopherol in meat due to higher concentrations in the high oil corn (Johnson, B. S., et. al., 2000. Impact of high oil corn on meat quality, J. Anim. Sci. 78, Supp. 1:155).

When dairy cows calve, their blood vitamin E concentrations drop drastically, and research shows that elevated levels of alpha-tocopherol (1000 to 4000 IU/kg/day) avoids this drop and reduces the incidence of mastitis (Weiss, W. P., et al., 1997. Effect of vitamin E supplementation in diets with a low concentration of selenium on mammary gland health of dairy cows, J. Dairy Science, 80(8): 1728–1737). In addition, any tocopherol fed to cows would be expected to extend the shelf life of milk under refrigeration, so addition of tocopherol may prove useful for retarding rancidity in milk and milk products. With beef, color stability improves until alpha-tocopherol concentrations reach 3 to 3.3 micrograms per gram of tissue. Based on the favorable results obtained from the lamb test, Applicants have determined that adding gamma-tocopherol to the diet of any ruminant, including beef and dairy cattle, will increase meat or milk shelf life and meat coloration. Dosage levels of gamma-tocopherol will be approximately equal to the effective dosage levels of alpha-tocopherol. For example, if one would normally use 100 ppm of alpha-tocopherol for a given effect, then about 100 ppm of gamma-tocopherol may be used either instead or in various combinations with alpha-tocopherol.

EXAMPLE 5

Sources of Gamma-Tocopherol

A promising source of gamma-tocopherol for animal feed supplementation is the oil seed processing industry. During oil seed processing, oil is first extracted from the seed, then the extracted oil is refined. The residue left from the refining deodorization step is often rich in gamma-tocopherol. This residue can be mixed with animal feed to add gamma-tocopherol to the diet. Oil seed distillate that may be utilized in the present invention include soybean, sesame, sunflower, flax, canola, corn, sorghum, cotton, palm, barley and millet. Those seeds not naturally high in gamma-tocopherol may be genetically modified to have increased levels of gamma-tocopherol as described below.

As used herein, the term deodorizer distillate includes deodorizer distillate that has been further purified, refined or derivatized. For example, further distillation will result in an increased concentration of gamma-tocopherol. It would also be preferable to strip pesticide residues by a high temperature distillation under vacuum. For example, one process for recovering tocopherols from deodorizer sludge is provided in U.S. Pat. No. 4,594,437.

Maize deodorizer distillate typically contains about 2–4% gamma-tocopherol by weight (on a dry weight basis, which excludes water) and other lipid-soluble material. Thus, to get the proper levels of gamma-tocopherol in the feed, one would use a feed comprising about 1% deodorizer distillate.

The remaining portion of the deodorizer distillate consists of free fatty acids, neutral oil, and unsaponifiable material including sterols and other tocopherol isomers.

Soybean deodorizer distillate has a tocopherol content of between about 1–15%. The tocopherol content is often between about 10–14% at a deodorization temperature of 274° C., 3–5% stripping steam, 5–7 mm absolute pressure, and a deodorization time of 15 minutes in a Votator semi-continuous deodorizer.

A second source of gamma-tocopherol is a derivative that has had the hydrophobic side chain removed, which is referred to as 6-hydroxy-2,7,8-trimethylchroman-2-carboxylic acid. For example, see Muka, K., et. al., Bull Chem. Soc. Jpn., 60 2163–2167, 1987, which is hereby incorporated by reference. This derivative is more water soluble than gamma-tocopherol and is useful in various applications.

A third source of gamma-tocopherol is the derivative gamma-tocopherol acetate, which is produced in substantially the same manner as alpha-tocopherol acetate. The production of alpha-tocopherol acetate is discussed in U.S. Pat. No. 2,723,278, incorporated herein by reference.

A fourth source of gamma-tocopherol is from grain that has been modified to contain a high level of gamma-tocopherol. One method of transgenically increasing the amount of total tocopherol in plants, thereby increasing the amount of gamma-tocopherol, is disclosed in Della Penna et al. International Patent Application No. WO 00/68393, incorporated herein by reference. The Della Penna et al. patent discloses isolating nucleic acids and their proteins involved in tocopherol biosynthesis for transformation of plant cells.

Della Penna et al. International Patent Application No. WO 99/04622, incorporated herein by reference, discloses enzymes for encoding gamma-tocopherol methyltransferases from plants. Gamma-tocopherol methyltransferase regulates the relative amounts of alpha and gamma-tocopherol in plants.

The transgenic alteration of gamma-tocopherol levels in plants taught by Della Penna has successfully increased gamma-tocopherol levels in certain plants by over two times their normal levels. Such an increase in corn and soybeans, for example, would yield an amount of gamma-tocopherol containing grain that when fed at normal levels would provide about 100 ppm of gamma-tocopherol per day. Even greater increases of gamma-tocopherol in plants are possible.

These and other sources of gamma-tocopherol, such as encapsulated or chemically derivatized gamma-tocopherol, may be used in the present invention.

Sources of alpha-tocopherol to be used in conjunction with the gamma-tocopherol in accordance with certain aspects of the present invention include, but are not limited to, natural and synthetic alpha-tocopherol, alpha-tocopherol acetate, 6-hydroxy-2,5,7,8 tetramethyl chroman-2-carboxylic acid and alpha-tocopherol as part of deodorizer distillate.

Other modifications and alternative embodiments of the invention are contemplated which do not depart from the spirit and scope of the invention as defined by the foregoing teachings and appended claims. It is intended that the claims cover all such modifications that fall within their scope.

We claim as our invention:

1. A method of improving the tissue quality of an animal, comprising feeding the animal a diet comprising 100 ppm to 4,000 ppm gamma-tocopherol.

2. The method of claim 1 wherein the gamma-tocopherol is in the form of a distillate obtained from oil seed processing.

3. The method of claim 2 wherein the tissue is meat and the quality of the meat is measured by a criteria selected from the group consisting of increased shelf life, increased pH, improved color score and reduced purge.

4. The method of claim 2 wherein the diet comprises between 150 ppm and 450 ppm gamma-tocopherol.

5. The method of claim 2 wherein the diet comprises about 300 ppm gamma-tocopherol.

6. The method of claim 2 wherein the diet further comprises alpha-tocopherol.

7. The method of claim 2 wherein the animal is a ruminant.

8. The method of claim 7 wherein the animal is cattle.

9. The method of claim 2 wherein the animal is a non-ruminant.

10. The method of claim 9 wherein the animal is swine or poultry.

11. The method of claim 2 wherein the amount of gamma-tocopherol in the animal tissue is at least two times greater than the concentration of gamma-tocopherol in tissue of a second control animal that has not been fed supplemental gamma-tocopherol.

12. The method of claim 2 wherein the amount of gamma-tocopherol in the animal tissue is at least five times greater than the concentration of gamma-tocopherol in tissue of a second control animal that has not been fed supplemental gamma-tocopherol.

13. The method of claim 2 wherein the amount of gamma-tocopherol in the animal tissue is at least ten times greater than the concentration of gamma-tocopherol in tissue of a second control animal that has not been fed supplemental gamma-tocopherol.

14. The method of claim 1 wherein the gamma-tocopherol is in the form of derivatives of gamma-tocopherol.

15. The method of claim 14 wherein the derivatives are 6-hydroxy-2,7,8-trimethylchroman-2-carboxylic acid or gamma-tocopherol acetate.

16. The method of claim 15 wherein the tissue is meat and the quality of the meat is measured by a criteria selected from the group consisting of increased shelf life, increased pH, improved color score value and reduced purge.

17. The method of claim 14 wherein the diet comprises between 150 ppm and 450 ppm gamma-tocopherol.

18. The method of claim 14 wherein the diet comprises about 300 ppm gamma-tocopherol.

19. The method of claim 14 wherein the diet further comprises alpha-tocopherol.

20. The method of claim 14 wherein the animal is a ruminant.

21. The method of claim 20 wherein the animal is cattle.

22. The method of claim 14 wherein the animal is a non-ruminant.

23. The method of claim 22 wherein the animal is swine or poultry.

24. The method of claim 14 wherein the amount of gamma-tocopherol in the animal tissue is at least two times greater than the concentration of gamma-tocopherol in tissue of a second control animal that has not been fed supplemental gamma-tocopherol.

25. The method of claim 14 wherein the amount of gamma-tocopherol in the animal tissue is at least five times greater than the concentration of gamma-tocopherol in tissue of a second control animal that has not been fed supplemental gamma-tocopherol.

26. The method of claim 14 wherein the amount of gamma-tocopherol in the animal tissue is at least ten times greater than the concentration of gamma-tocopherol in tissue of a second control animal that has not been fed supplemental gamma-tocopherol.

27. The method of claim 1 wherein the gamma-tocopherol is fed in the form of grain from a transgenic plant modified to have increased gamma-tocopherol.

28. The method of claim 27 wherein the tissue is meat and the quality of the meat is measured by a criteria selected from the group consisting of increased shelf life, increased pH, improved color score value and reduced purge.

29. The method of claim 27 wherein the diet comprises between 150 ppm and 450 ppm gamma-tocopherol.

30. The method of claim 27 wherein the diet comprises about 300 ppm gamma-tocopherol.

31. The method of claim 27 wherein the diet further comprises alpha-tocopherol.

32. The method of claim 27 wherein the animal is a ruminant.

33. The method of claim 32 wherein the animal is cattle.

34. The method of claim 27 wherein the animal is a non-ruminant.

35. The method of claim 34 wherein the animal is swine or poultry.

36. The method of claim 27 wherein the amount of gamma-tocopherol in the animal tissue is at least two times greater than the concentration of gamma-tocopherol in tissue of a second control animal that has not been fed supplemental gamma-tocopherol.

37. The method of claim 27 wherein the amount of gamma-tocopherol in the animal tissue is at least five times greater than the concentration of gamma-tocopherol in tissue of a second control animal that has not been fed supplemental gamma-tocopherol.

38. The method of claim 27 wherein the amount of gamma-tocopherol in the animal tissue is at least ten times greater than the concentration of gamma-tocopherol in tissue of a second control animal that has not been fed supplemental gamma-tocopherol.

* * * * *